US011351528B2

(12) United States Patent
Jongkind et al.

(10) Patent No.: US 11,351,528 B2
(45) Date of Patent: Jun. 7, 2022

(54) CATALYST SYSTEM FOR DEWAXING

(71) Applicant: SHELL OIL COMPANY, Houston, TX (US)

(72) Inventors: Hermanus Jongkind, Amsterdam (NL); Marcello Stefano Rigutto, Amsterdam (NL); Erik Zuidema, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 0 days.

(21) Appl. No.: 17/047,987

(22) PCT Filed: Apr. 5, 2019

(86) PCT No.: PCT/EP2019/058673
§ 371 (c)(1),
(2) Date: Oct. 15, 2020

(87) PCT Pub. No.: WO2019/201627
PCT Pub. Date: Oct. 24, 2019

(65) Prior Publication Data
US 2021/0162383 A1 Jun. 3, 2021

(30) Foreign Application Priority Data
Apr. 17, 2018 (EP) .................................... 18167764

(51) Int. Cl.
B01J 29/80 (2006.01)
B01J 29/70 (2006.01)
(Continued)

(52) U.S. Cl.
CPC ............... B01J 29/80 (2013.01); B01J 23/38 (2013.01); B01J 29/703 (2013.01);
(Continued)

(58) Field of Classification Search
CPC ...... B01J 29/703; B01J 29/7034; B01J 29/80; C10G 45/62–64; C10G 47/20
See application file for complete search history.

(56) References Cited

U.S. PATENT DOCUMENTS 3,140,249 A 7/1964 Plank et al.
3,140,251 A 7/1964 Plank et al.
(Continued)

FOREIGN PATENT DOCUMENTS

CA 2694898 A1 2/2009
CN 1703493 A 11/2005
(Continued)

OTHER PUBLICATIONS

International Search Report and Written Opinion received for PCT Patent Application No. PCT/EP2019/058673 dated Jul. 2, 2019, 8 pages.
(Continued)

Primary Examiner — Renee Robinson
(74) Attorney, Agent, or Firm — Shell USA, Inc.

(57) ABSTRACT

A catalyst system for dewaxing of a hydrocarbon feedstock comprising a mixture of a first dewaxing catalyst composition and a second dewaxing catalyst composition, wherein the first dewaxing catalyst composition is a ZSM-12 zeolite based catalyst composition and the second dewaxing catalyst composition is a EU-2 and/or ZSM-48 zeolite based catalyst composition, and wherein a concentration gradient of the mixture is achieved within a single catalyst bed, such that the concentration of the first dewaxing catalyst is decreasing and the concentration of the second dewaxing catalyst is increasing through the catalyst bed; and a process for dewaxing of a hydrocarbon feedstock comprising contacting the hydrocarbon feedstock with said catalyst system.

10 Claims, 1 Drawing Sheet

(51) Int. Cl.
*C10G 45/64* (2006.01)
*B01J 23/38* (2006.01)
*C10G 47/20* (2006.01)

(52) U.S. Cl.
CPC .......... *B01J 29/7034* (2013.01); *C10G 45/64* (2013.01); *C10G 47/20* (2013.01)

(56) References Cited

U.S. PATENT DOCUMENTS

| | | |
|---|---|---|
| 3,140,253 A | 7/1964 | Plank et al. |
| 3,832,449 A | 8/1974 | Rosinski et al. |
| 4,205,053 A | 5/1980 | Rollmann et al. |
| 4,391,785 A | 7/1983 | Rosinki et al. |
| 4,452,769 A | 6/1984 | Chu et al. |
| 4,482,531 A | 11/1984 | Kuehl |
| 4,539,193 A | 9/1985 | Valyocsik |
| 4,552,738 A | 11/1985 | Rubin |
| 4,552,739 A | 11/1985 | Kuehl |
| 4,585,637 A | 4/1986 | Rubin |
| 4,585,746 A | 4/1986 | Valyocsik |
| 4,599,162 A | 7/1986 | Fen |
| 4,741,891 A | 5/1988 | Casci et al. |
| 4,753,910 A | 6/1988 | Han et al. |
| 4,767,522 A | 8/1988 | Yen |
| 5,021,141 A | 6/1991 | Rubin |
| 5,075,259 A | 12/1991 | Moran |
| 5,075,269 A | 12/1991 | Degnan et al. |
| 5,080,878 A | 1/1992 | Bowes et al. |
| 5,157,191 A | 10/1992 | Bowes et al. |
| 5,192,521 A | 3/1993 | Moini et al. |
| 5,234,872 A | 8/1993 | Apelian et al. |
| 5,242,676 A | 9/1993 | Apelian et al. |
| 5,246,568 A | 9/1993 | Forbus et al. |
| 5,430,000 A | 7/1995 | Timken |
| 6,051,129 A | 4/2000 | Harris et al. |
| 6,576,120 B1 | 6/2003 | Van Ballegoy et al. |
| 6,652,832 B2 | 11/2003 | Malek |
| 6,893,624 B2 | 5/2005 | Lai et al. |
| 7,261,805 B2 | 8/2007 | Grove et al. |
| 2004/0082461 A1 | 4/2004 | Remans et al. |
| 2004/0108245 A1 | 6/2004 | Jiang et al. |
| 2007/0138060 A1 | 6/2007 | Palmer et al. |
| 2009/0166252 A1 | 7/2009 | Daage et al. |
| 2009/0176643 A1 | 7/2009 | Elia et al. |
| 2009/0186754 A1 | 7/2009 | Elia et al. |
| 2010/0075831 A1 | 3/2010 | Elia et al. |
| 2011/0034759 A1 | 2/2011 | Ogdahl et al. |
| 2011/0118520 A1 | 5/2011 | Lai et al. |
| 2013/0153463 A1 | 6/2013 | Geerinck et al. |
| 2014/0209506 A1 | 7/2014 | Domokos et al. |
| 2017/0306251 A1* | 10/2017 | Kim .................. B01J 29/7261 |
| 2017/0369794 A1 | 12/2017 | Renkema et al. |
| 2020/0094231 A1 | 3/2020 | Jongkind et al. |

FOREIGN PATENT DOCUMENTS

| | | |
|---|---|---|
| CN | 1989089 A | 6/2007 |
| EP | 0188898 A2 | 7/1986 |
| EP | 2075314 A1 | 7/2009 |
| EP | 3239276 A1 | 11/2017 |
| GB | 2077709 A | 12/1981 |
| RU | 2177468 C2 | 12/2001 |
| WO | 9641846 A1 | 12/1996 |
| WO | 9641849 A1 | 12/1996 |
| WO | 0029512 A1 | 5/2000 |
| WO | 2005092792 A1 | 10/2005 |
| WO | 2007070521 A1 | 6/2007 |
| WO | 2010053468 A1 | 5/2010 |
| WO | 2012055755 A1 | 5/2012 |
| WO | 2013090534 A1 | 6/2013 |

OTHER PUBLICATIONS

International Search Report and Written Opinion received for PCT Patent Application No. PCT/EP2011/068329 dated Dec. 8, 2011, 10 pages.
International Search Report and Written Opinion received for PCT Patent Application No. PCT/US2012/069438 dated Mar. 6, 2013, 10 pages.
International Search Report and Written Opinion received for PCT Patent Application No. PCT/EP2011/068345 dated Dec. 13, 2011, 9 pages.
International Search Report and Written Opinion received for PCT Patent Application No. PCT/EP2017/082643 dated Apr. 13, 2018, 10 pages.
Database of Zeolite Structures, Framework Type MTW, 2007, Structure Commission of International Zeolite Association.
Porter et al., "The Effect of Calcination on the Microstructural Characteristics and Photoreactivity of Degussa P-25 Tio2", Journal of Materials Science, vol. 34, Issue No. 7, 1999, pp. 1523-1531.
Catalog of Disorder in Zeolite Frameworks, Database of Zeolite Structures, 2000, 3 pages.

* cited by examiner

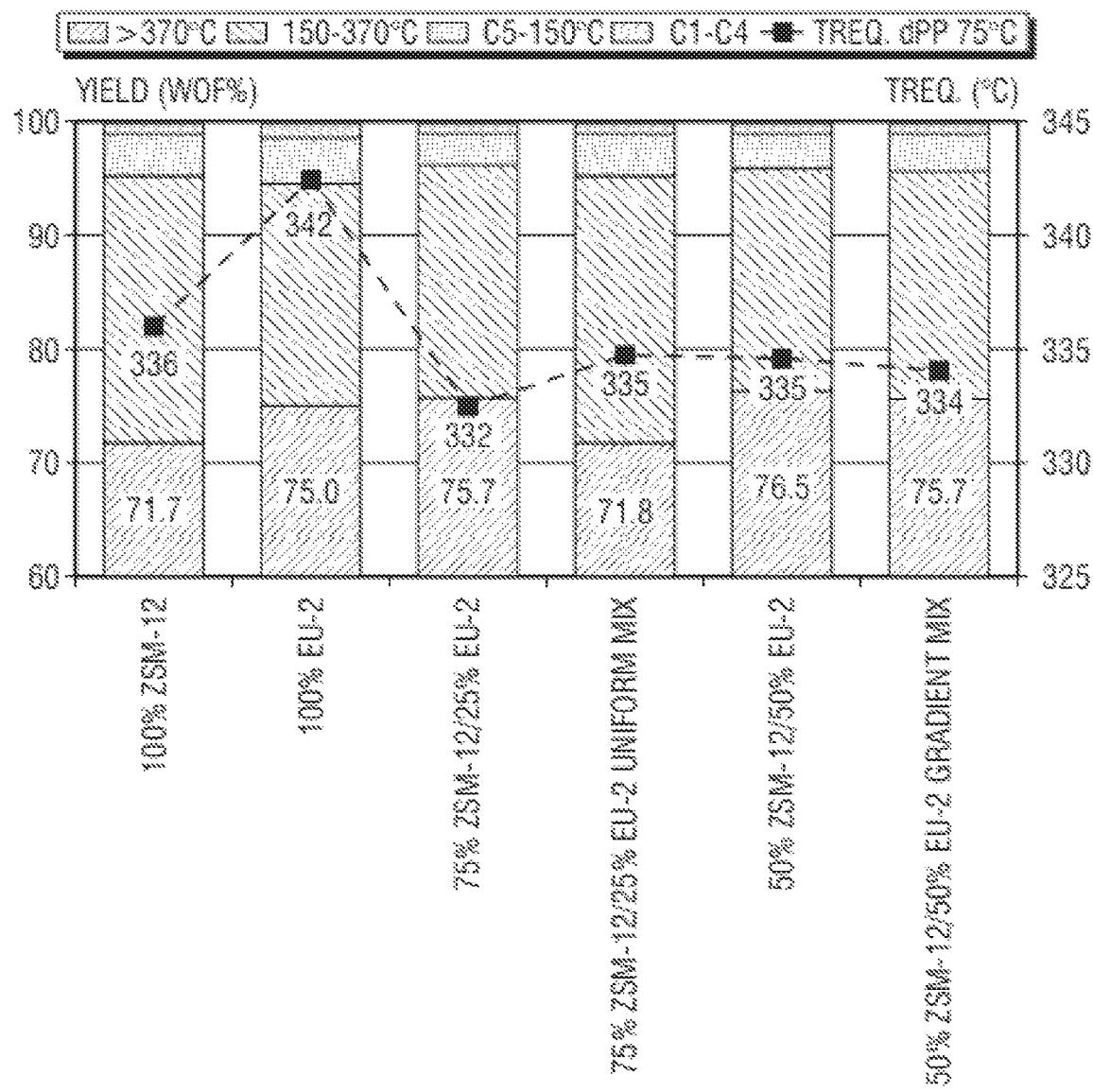

CATALYST SYSTEM FOR DEWAXING

CROSS REFERENCE TO RELATED APPLICATIONS

This is a national stage application of International Application No. PCT/EP2019/058673, filed 5 Apr. 2019, which claims benefit of priority to European Patent Application No. 18167764.2, filed 17 Apr. 2018.

The invention relates to catalyst system for dewaxing of a hydrocarbon feedstock comprising a ZSM-12 zeolite based catalyst and a EU-2 and/or ZSM-48 zeolite based catalyst, and a process for converting a hydrocarbon feedstock using said catalyst system.

BACKGROUND OF THE INVENTION

There are ongoing efforts to provide improved catalysts for use in the catalytic dewaxing of hydrocarbon feedstocks. Such improvements may include dewaxing catalysts having enhanced activity or which provide for improved lube stock yields when processing certain hydrocarbon feedstocks. Several types of zeolites have been developed for that purpose. For example, in WO 2012/055755 A and WO 2012/055759 A certain specific ZSM-48 and/or EU-2 zeolite based catalysts are described displaying improved hydrocarbon conversion performance. As described in the Catalog of Disorder in Zeolite Frameworks published in 2000, both ZSM-48 and EU-2 zeolite belong to the family of ZSM-48 zeolites. Therefore, in this text, where ZSM-48 is mentioned, also EU-2 can be read, and vice versa. Another zeolite, the crystalline zeolite designated ZSM-12, is described in U.S. Pat. No. 3,832,449 A. ZSM-12 zeolites are indicated in the '449 patent as having catalytic characteristics being useful in petroleum refining processes that include processes for the reduction of the pour point of paraffinic charge stocks and the isomerization of n-paraffins and naphthenes.

There is a constant need for more active and/or selective catalysts for catalytic dewaxing of hydrocarbon feedstocks. In order to arrive at increased activity, it is not uncommon to increase the zeolite content of catalysts. However, that is accompanied by higher costs of materials of the catalysts.

Other solutions have also been considered. For example, U.S. Pat. No. 4,599,162 A describes a dual catalyst cascade process for dewaxing of hydrocarbon feedstocks, in which the waxy feedstock is passed over a crystalline silicate zeolite catalyst having a Constraint Index between 2 and 12 and then over a different crystalline silicate zeolite catalyst having a Constraint Index no less than 2.

Specifically, said patent is directed to a cascade catalytic hydrodewaxing process comprising (a) passing a hydrocarbon feedstock containing waxy components selected from a group of normal paraffins and slightly branched chain paraffins over a hydroisomerization catalyst comprising a crystalline silicate zeolite having the structure ZSM-12 in admixture with a crystalline silicate zeolite having the structure of ZSM-23, said admixture having hydrogenation/dehydrogenation activity to hydroisomerise the feedstock; and (b) passing at least a majority of the normally liquid hydrocarbon recovered from step (a) over a de-waxing catalyst comprising a crystalline silicate zeolite having a structure of ZSM-5, said zeolite of step (b) having hydrogenation/dehydrogenation activity to dewax the recovered hydrocarbon.

Examples in U.S. 4,599,162 A utilise a dual catalyst operation, wherein in a first reactor zone, a catalyst comprising 0.44% Pt/ZSM-12 and ZSM-23 in admixture is employed, whilst in a second reactor zone, a catalyst comprising a Ni/ZSM-5 based catalyst is employed. The results reported in Table 2 of U.S. Pat. No. 4,599,162 A however indicate a significant gas make (C1-C5 yield range from 7.4 to 9.8 wt. %), which is disadvantageous for the base oil.

Further, in U.S. Pat. No. 7,261,805 B2 a process is described for upgrading a hydrocarbon feedstock containing waxy components and having an end boiling point exceeding 650° F. (343° C.), which includes contacting the feedstock at superatmospheric hydrogen partial pressure with an isomerization dewaxing catalyst that includes ZSM-48 and then contacting the dewaxed product with a hydrocracking catalyst to produce an upgraded product with a reduced wax content. The product of the process of the '805 patent is a distillate having a boiling range of about 330° F. (166° C.) to 730° F. (387° C.).

Co-pending patent application PCT/EP2017/082643 discloses a stacked catalyst system for dewaxing of a hydrocarbon feedstock, said catalyst system comprising a ZSM-12 based catalyst in the top of the stack and a EU-2 (ZSM-48) based catalyst in the bottom of the stack. Said catalyst system exhibits both enhanced performance and an improved base oil yield when compared to catalyst systems containing only a ZSM-12 or a EU-2(ZSM-48) based catalyst, respectively.

Despite all advances that already have been made in catalyst dewaxing, there is still a continued need for new developments having advantageous catalyst performance, preferably also with attractive base oil yields and selectivity for certain product ranges, while still being economically attractive. It is an object of the present invention to present additional beneficial catalyst systems for dewaxing of hydrocarbon feedstocks.

SUMMARY OF THE INVENTION

It has now been found that improved catalyst performance in terms of an enhanced selectivity and/or a higher catalyst activity can be effected in another way than suggested in the prior art.

Surprisingly, it has now been found that a catalyst system comprising a graduated mixture of ZSM-12 based catalyst and a EU-2 (ZSM-48) based catalyst, that is to say, a mixture having a concentration gradient of said catalysts in the catalyst bed, exhibits both enhanced performance and an improved base oil yield when compared to catalyst systems containing only a ZSM-12 or a EU-2(ZSM-48) based catalyst, respectively.

Accordingly, the present invention provides a catalyst system for dewaxing of a hydrocarbon feedstock comprising a mixture of a first dewaxing catalyst composition and a second dewaxing catalyst composition, wherein the first dewaxing catalyst composition is a ZSM-12 zeolite based catalyst composition and the second dewaxing catalyst composition is a EU-2 and/or ZSM-48 zeolite based catalyst composition, and wherein a concentration gradient of the mixture is achieved within a single catalyst bed, such that the concentration of the first dewaxing catalyst is decreasing and the concentration of the second dewaxing catalyst is increasing through the catalyst bed.

The catalyst system of the invention is particularly useful for the production of base oils. Accordingly, the present invention also provides a process for dewaxing of a hydrocarbon feedstock comprising contacting the hydrocarbon feedstock with a catalyst system according to the present invention.

DETAILED DESCRIPTION OF THE INVENTION

The ZSM-12 zeolite based catalyst composition used in the catalyst system of this invention can, for example, be made according to procedures described for comparative catalyst composition A in WO 2013/090534 A.

In a preferred embodiment of the present invention, the ZSM-12 zeolite based catalyst composition does not contain any additional zeolites therein.

An important feature of the ZSM-12 zeolite component is to have a silica-to-alumina ratio that is sufficiently high to provide for a dewaxing catalyst composition that exhibits desired catalytic properties of high activity while providing for a high yield. To provide for this, the ZSM-12 zeolite component preferably has a silica-to-alumina ratio (also referred to sometimes herein as "SAR"; units are mol:mol) that is at least 50:1. The silica-to-alumina ratio, as the term is used herein, references the molar ratio of silica and alumina contained in the framework of the zeolite. Preferably, the SAR is greater than 60:1, or greater than 70:1, or greater than 75:1. An upper limit to the SAR of the ZSM-12 zeolite component is preferably at most 250:1, more preferably, the upper limit is at most 200:1, and more preferably less than 150:1, in particular less than 110:1. If the SAR of the as-synthesized ZSM-12 zeolite is too low, it may further dealuminated using methods known in the art to provide a dealuminated ZSM-12 zeolite having the desired silica-to-alumina ratio that can be used as a component of the inventive catalyst system.

The ZSM-12 zeolite content of the first dewaxing catalyst composition may conveniently be at least 10 wt. % and at most 70 wt. % of the total dry weight of the first dewaxing catalyst composition. It is preferred for the ZSM-12 zeolite content of the first dewaxing catalyst composition to be at most 60 wt. %, more preferred, at most 50 wt %, and more in particular at most 40 wt. %. It is further preferred for the ZSM-12 zeolite content of the first dewaxing catalyst composition to be at least 15 wt. %, and more preferred, at least 20 wt. %.

The binder content of the first dewaxing catalyst composition used in the catalyst system of the invention may conveniently be in the range of from at least 30 wt. % and no more than 90 wt. % of the total dry weight of the first dewaxing catalyst composition.

The EU-2/ZSM-48 zeolite based catalyst composition used in the catalyst system of the present invention can, for example, be made according to procedures described in WO 2012/055755 A for dealuminated ZSM-48 and/or EU-2 zeolite based catalysts comprising a refractory oxide binder essentially free of alumina. The SAR of the EU-2 and/or ZSM-48 zeolite preferably is at least 60:1, more preferably at least 70:1, more preferably at least 80:1, most preferably at least 90:1. The SAR of the EU-2 and/or ZSM-48 zeolite preferably is at most 300:1, more preferably at most 250:1, even more preferably at most 200:1, and most preferably at most 150:1.

When contents of binder and zeolite are used in the context of the present invention, the content on a dry basis is meant. The EU-2/ZSM-48 zeolite content of the second dewaxing catalyst composition is preferably at most 70% by weight (wt. %), more preferably at most 65 wt. %, even more preferably at most 60 wt. %, and most preferably at most 55 wt. % of the total dry weight of the second dewaxing catalyst composition. Further, it is preferred that the amount of EU-2/ZSM-48 zeolite is at least 15 wt. %, more preferably at least 20 wt. %, even more preferably at least 25 wt. %, and most preferably at least 30 wt. % of the total dry weight of the second dewaxing catalyst composition.

Optionally, a further zeolite may be present in the second dewaxing catalyst composition besides the EU-2/ZSM-48 zeolite; if that is the case, such zeolite preferably is present in an amount of at most 50 wt. %, based on the amount of EU-2/ZSM-48 zeolite that is present.

The binder content of the second dewaxing catalyst composition used in the catalyst system of the present invention may conveniently be in the range of from at least 30 wt. % and no more than 85 wt. % of the total dry weight of the second dewaxing catalyst composition.

When reference is made to binders herein, refractory oxide binders are meant. Examples of refractory oxide binder materials are alumina, silica, zirconia, titanium dioxide, germanium dioxide, boria and mixtures of two or more of these like for example silica-zirconia and silica-titania. Preferred binders are titania, zirconia and/or silica. Silica is a particularly preferred binder in the ZSM-12 zeolite based catalyst composition and the EU-2/ZSM-48 zeolite based catalyst composition used in the catalyst system of the present invention.

The ZSM-12 zeolite based catalyst composition and the EU-2/ZSM-48 zeolite based catalyst composition used in the catalyst system of the present invention, further preferably each comprise a noble metal component which is more preferably selected from the group of noble metals consisting of palladium and platinum. The most preferred noble metal, however, is platinum for both the ZSM-12 zeolite based catalyst composition and the EU-2/ZSM-48 zeolite based catalyst composition. The noble metal component is preferably incorporated into the mixture or particle after its treatment or dealumination. However, the noble metal component may also be incorporated into the mixture or particle before treatment or dealumination. Any known suitable means or method may be used to incorporate the noble metal component into the mixture or particle.

It is desirable for the ZSM-12 zeolite based catalyst composition and the EU-2/ZSM-48 zeolite based catalyst composition used in the catalyst system of the invention to each have a noble metal content in the range of upwardly to about 3 wt. %, based on the noble metal as an element, regardless of its actual form, and the total dry weight of the respective catalyst composition. It is preferred for the noble metal component to be present in the respective catalyst compositions at a concentration in the range of from 0.1 wt. % to 3 wt. %, based on the noble metal as an element, regardless of its actual form, and the total dry weight of the respective catalyst composition. More preferably, the noble metal component is present in each of the respective catalyst compositions in an amount in the range of from 0.2 wt. % to 2 wt. %, and, most preferably, it is in the range of from 0.3 wt. % to 1 wt. %, based on the noble metal as an element, regardless of its actual form, and the total dry weight of the respective catalyst composition.

The ZSM-12 and EU-2/ZSM-48 based zeolite catalyst compositions are further extruded, dried and calcined according to methods known in the art.

As hereinbefore described, the present invention provides a catalyst system for dewaxing of a hydrocarbon feedstock, wherein said catalyst system comprises a graduated mixture of the first dewaxing catalyst composition (i.e. the ZSM-12 zeolite based catalyst composition) and the second dewaxing catalyst composition (i.e. the EU-2 and/or ZSM-48 zeolite based catalyst composition) in the catalyst bed.

By "graduated mixture" in the present invention is meant that there is a concentration gradient of the mixture of first and second dewaxing catalysts throughout the catalyst bed or beds. It will be appreciated that the afore-mentioned concentration gradient may be achieved within a single catalyst bed (such that the concentration of the first dewaxing catalyst is decreasing and the concentration of the second dewaxing catalyst is increasing through the catalyst bed in either a linear or non-linear fashion) or the concentration gradient may be achieved in separate catalyst beds, in separate reactors or multiple reactors, such that the concentration of the first dewaxing catalyst (i.e. the ZSM-12 zeolite based catalyst composition) is decreasing and the concentration of the second dewaxing catalyst (i.e. the EU-2 and/or ZSM-48 zeolite based catalyst composition) is increasing in a non-linear fashion in moving from one catalyst bed to the next.

In the present invention, it is preferred that the afore-mentioned concentration gradient of the mixture is achieved within a single catalyst bed, such that the concentration of the first dewaxing catalyst is decreasing and the concentration of the second dewaxing catalyst is increasing through the catalyst bed. The decreases and increases in concentrations of the first and second dewaxing catalyst compositions, respectively, through the catalyst bed may be in either a linear or non-linear fashion.

By "through the catalyst bed" is meant in moving from the inlet to the outlet of the catalyst bed.

Accordingly, in the present invention, it is preferred that the concentration of the first dewaxing catalyst composition (i.e. the ZSM-12 zeolite based catalyst composition) is highest at the inlet or inlet region of the catalyst bed (e.g., for a reactor in top-down flow, this will be in the upper region of the catalyst bed which first comes into contact with the hydrocarbon feedstock) and the concentration of the second dewaxing catalyst composition (i.e. the EU-2 and/or ZSM-48 zeolite based catalyst composition) is highest at the outlet or outlet region of the catalyst bed (e.g., for a reactor in top-down flow, this will be in the lower region or bottom of the catalyst bed).

In one embodiment of the present invention, the concentration gradient of the mixture of first and second dewaxing catalysts through the catalyst bed may be such that there is a linear decrease in the concentration of first dewaxing catalyst composition (i.e. the ZSM-12 zeolite based catalyst composition) through the catalyst system from the inlet (i.e. the region or regions of the catalyst bed which first come into contact with the hydrocarbon feedstock) to the outlet of the catalyst bed and there is a linear increase in the concentration of second dewaxing catalyst composition (i.e. the EU-2 and/or ZSM-48 zeolite based catalyst composition) through the catalyst system from the inlet (i.e. the region or regions of the catalyst bed which first come into contact with the hydrocarbon feedstock) to the outlet of the catalyst bed.

In a preferred embodiment of the present invention, the catalyst bed comprises two or more separate regions in a stacked configuration, each region comprising a mixture of the first and second dewaxing catalysts (i.e. the ZSM-12 zeolite based catalyst composition and the EU-2 and/or ZSM-48 zeolite based catalyst composition), such that the regions together define a gradient decreasing in the concentration of the first dewaxing catalyst composition and increasing in the concentration of second dewaxing catalyst composition (i.e. the EU-2 and/or ZSM-48 zeolite based catalyst composition) in a step-wise, non-linear, fashion from one region to the next region through the catalyst bed.

In one embodiment of the present invention, the catalyst system may optionally comprise a first (inlet) region of the catalyst bed consisting essentially of the first dewaxing catalyst (i.e. the ZSM-12 zeolite based catalyst composition) and/or final (outlet) region of the catalyst bed consisting essentially of the second dewaxing catalyst composition (i.e. the EU-2 and/or ZSM-48 zeolite based catalyst composition).

In the present invention, it has been surprisingly found that higher base oil yields are obtained using the arrangement employed in the catalyst system of the present invention, as compared to using a homogeneous, non-gradient mixture of first dewaxing catalyst (i.e. the ZSM-12 zeolite based catalyst composition) and the second dewaxing catalyst composition (i.e. the EU-2 and/or ZSM-48 zeolite based catalyst composition), that is to say, wherein the catalyst bed contains a uniform (constant) concentration of the first and second dewaxing catalysts (i.e. the ZSM-12 zeolite based catalyst composition and the EU-2 and/or ZSM-48 zeolite based catalyst composition, respectively) through the catalyst bed.

In the catalyst system of the present invention, the overall catalyst volume ratio of the first dewaxing catalyst to the second dewaxing catalyst preferably is in the range of 10:90 to 90:10. More preferred, that ratio is from 20:80 to 90:10, even more preferred from 40:60 to 85:15. A highly preferred overall catalyst volume ratio of the first dewaxing catalyst to the second dewaxing catalyst is 75:25.

In embodiments of the present invention, wherein the catalyst bed comprises two or more separate regions in a stacked configuration, each region comprising a mixture of the first and second dewaxing catalysts (i.e. the ZSM-12 zeolite based catalyst composition and the EU-2 and/or ZSM-48 zeolite based catalyst composition), then each region in the stacked configuration may separately have a catalyst volume ratio of the first dewaxing catalyst to the second dewaxing catalyst therein in the range of 10:90 to 90:10, more preferably in the range of from 20:80 to 90:10, even more preferably from 40:60 to 85:15, provided that the regions together define a gradient decreasing in the concentration of the first dewaxing catalyst composition and increasing in the concentration of second dewaxing catalyst composition (i.e. the EU-2 and/or ZSM-48 zeolite based catalyst composition) from one region to the next region through the catalyst bed.

The catalyst system of the present invention may be prepared using conventional methods and conventional means.

Dependent upon the nature of the linear or non-linear concentration gradient required, a number of discreet mixtures of the first and second dewaxing catalyst compositions in varying ratios of first to second catalyst composition may be prepared.

Said mixtures are then loaded into the catalyst bed to achieve a mixture of the first and second catalyst compositions having the desired concentration gradient.

Any type of reactor (e.g. a reactor in top-down or bottom-up flow) may be loaded in such a way that the feed will pass through the afore-mentioned catalyst bed comprising a mixture of the first and second dewaxing catalysts as hereinbefore described, wherein a concentration gradient of the mixture is achieved within the catalyst bed, such that the concentration of the first dewaxing catalyst is decreasing and the concentration of the second dewaxing catalyst is increasing through the catalyst bed. When, for example, an industrial reactor is operated in a top-down flow, the preparation of the catalyst system will result in higher concentrations of the first dewaxing catalyst composition (i.e. the ZSM-12 zeolite based catalyst composition) in the top or upper regions of the catalyst bed than in the bottom or lower regions of the catalyst bed, which will have higher concentrations of the second dewaxing catalyst composition (i.e. the EU-2 and/or ZSM-48 zeolite based catalyst composition).

For completeness, it must be mentioned that below the catalyst system of the present invention, another catalyst can be present for, e.g. hydrofinishing purposes.

For commercial units various loading techniques are available which are often executed by specialised companies (like the Dutch company "Mourik").

The catalyst system of the present invention is highly suitable for use in dewaxing of hydrocarbon feedstocks. The system can be placed as the dewaxing section in any conventional line up comprising a section for dewaxing of hydrocarbon feedstocks.

In a preferred embodiment of the present invention, the hydrocarbon feedstock may be pre-treated upstream of the catalyst system, for example, in a separate guard or catalyst bed, to reduce or remove any nitrogen- and sulfur-containing compounds and/or aromatic compounds present therein. Alternatively, a further catalyst may be used upstream of the catalyst system of the present invention in the same reactor bed in order to pre-treat the feedstock prior to contact with said catalyst system.

Catalytic dewaxing is used to improve cold flow properties of diesel fuels and lube oils by selective hydroisomerization/hydrocracking of normal and slightly branched paraffins. In distillate dewaxing, the dewaxing process reduces the pour point of the feedstock preferably by at least 10° C., more preferably by at least 20° C. The current catalyst system may be used for conventional diesel fuels dewaxing to deep dewaxing (Artic grade production) in first and second stage applications, in combination with high pressure hydrocracking or mild hydrocracking catalyst package, in mild hydrocracker bottoms pour point reduction for storage and transportation and/or to produce lubes of exceptional quality. The catalyst system of the present invention is particularly useful for producing base oils.

Accordingly, the present invention further relates to a process for dewaxing of a hydrocarbon feedstock comprising contacting a hydrocarbon feedstock with a catalyst system of the invention at an elevated temperature, preferably from 200° C. up to 450° C. and a pressure of from $5 \times 10^5$ to $200 \times 10^5$ Pa. More preferably, the temperature is from 250 to 400° C., preferably of from 275 to 375° C. The total pressure is more preferably of from $15 \times 10^5$ to $170 \times 10^5$ Pa, preferably of from $25 \times 10^5$ to $150 \times 10^5$ Pa.

In the dewaxing process of the present invention, the liquid hourly space velocity of the hydrocarbon feedstock is preferably in the range of from 0.1 to 10 $h^{-1}$.

Suitable hydrocarbon oil feeds to be employed in the dewaxing process according to the present invention are mixtures of high-boiling hydrocarbons, such as, for instance, heavy oil fractions. It has been found particularly suitable to use vacuum distillate fractions derived from an atmospheric residue, i.e. distillate fractions obtained by vacuum distillation of a residual fraction which in return is obtained by atmospheric distillation of a crude oil, as the feed. The boiling range of such a vacuum distillate fraction is usually between 300 and 620° C., suitably between 350 and 580° C. However, deasphalted residual oil fractions, including both deasphalted atmospheric residues and deasphalted vacuum residues, may also be applied. The feedstock to be subjected to dewaxing preferably is a gas oil or a lube oil basestock.

Thus, in one embodiment, the feedstocks are wax-containing feeds that boil in range usually between 130 and 450° C., suitably between 150 and 390° C. These are the boiling ranges for diesel, kerosene and jet fuel.

In a preferred embodiment, the feedstock is a lube oil basestock. Such feedstocks preferably are wax-containing feeds that boil in the lubricating oil range typically having a 10% distillation point at 200° C. or higher, ranging to 600° C., as measured by ASTM D-2887-93. Examples of feeds having relatively high amounts of waxy compounds are synthetic waxy raffinates (Fischer-Tropsch waxy raffinates), hydrocracker bottom fractions (hydrowax), i.e. those fractions having a final boiling point of at least 320° C., preferably at least 360° C. and slack waxes obtained from the dewaxing of hydroprocessed or solvent refined waxy distillates. These feeds have a wax content of at least 50% by weight, preferably at least 80% by weight and more preferably at least 90% by weight. The wax content is the content of compounds which are plastic at ambient temperature and melt above 45° C. to give a low viscosity liquid. The amount of wax can be determined by the ASTM method D3235.

If a feedstock contains substantial amounts of sulphur- and/or nitrogen-containing contaminants, for example, having sulphur levels up to 3% by weight and nitrogen levels up to 1% by weight, it may be advantageous to subject that feedstock to a hydro-desulphurisation and hydrodenitrogenation step prior to the catalytic dewaxing process using the catalytic system of the present invention.

The process of the present invention can be used to prepare lubricating base oils having viscosity indices (VI) above 120 and particularly above 135.

Furthermore, the feedstocks may have been hydrotreated and/or hydrocracked before being subjected to dewaxing. Hydrotreating generally involves contacting feedstock with a hydrotreating catalyst at a temperature of up to 500° C., more preferably of from 250 to 500° C., and a hydrogen partial pressure of from $10 \times 10^5$ to $200 \times 10^5$ Pa, more preferably of from $30 \times 10^5$ to $130 \times 10^5$ Pa. Hydrocracking generally involves contacting feedstock with a hydrocracking catalyst at a hydrogen partial pressure (at the reactor inlet) in the range from $3 \times 10^6$ to $2.9 \times 10^7$ Pa, more preferably from $8 \times 10^6$ to $1.75 \times 10^7$ Pa and a ratio of hydrogen gas to feedstock (total gas rate) in the range from 100 to 5000 Nl/kg, but preferably in the range from 200 to 3000 Nl/kg.

BRIEF DESCRIPTION OF THE DRAWING

FIG. 1 shows performance data of catalyst systems tested.
The method of the invention will now be illustrated by the following non-limiting examples.

EXAMPLES

Example 1. ZSM-12 Composition

An extrudable mass was prepared by combining ZSM-12 zeolite having a SAR of 90 from Zeolyst International with amorphous silica, ammonia and water. The mass was extruded to give extrudates having a cylinder shape and an average diameter of 1.6 mm. These extrudates were dried and calcined resulting in white extrudates.

The extrudates were treated unstirred at a temperature of 90° C. for 5 hours with aqueous ammonium hexafluorosilicate (AHS) solution. The weight ratio of solution to extrudates was 5:1. Subsequently, the extrudates were separated from the solution, washed with deionized water, and dried and calcined.

Thereafter, 0.7% wt./wt. platinum was incorporated into the composition by pore volume impregnation during about 10 minutes with an aqueous solution containing tetramine platinum nitrate ($Pt(NH_3)_4(NO_3)_2$) (3.37% wt./wt. Pt).

The impregnated composition was not washed, but equilibrated during 1.5 hours on a rolling bed, dried and calcined. Then, the catalyst was cooled down to room temperature.

Example 2. EU-2 (ZSM-48) Composition

Zeolite EU-2 (ZSM-48) having a SAR of 110 was prepared as described in U.S. Pat. No. 4,741,891 A. An extrudable mass was prepared by combining EU-2 with amorphous silica, ammonia and water. The mass was extruded to give extrudates having a cylinder shape and an average diameter of 1.6 mm. These extrudates were dried and calcined resulting in white extrudates.

The extrudates were treated unstirred at a temperature of 90° C. for 5 hours with aqueous ammonium hexafluorosilicate (AHS) solution. The weight ratio of solution to extrudates was 5:1. Subsequently, the extrudates were separated from the solution, washed with deionized water, and dried and calcined.

Thereafter, 0.7% wt./wt. platinum was incorporated into the composition by pore volume impregnation during about 10 minutes with an aqueous solution containing tetramine platinum nitrate ($Pt(NH_3)_4(NO_3)_2$) (3.3% wt./wt. Pt).

The impregnated composition was not washed, but equilibrated during 1.5 hours on a rolling bed, dried and calcined. Then, the catalyst was cooled down to room temperature.

Example 3. Performance Testing of Comparative Single Bed and Stacked Bed Catalyst Systems The catalysts of Examples 1 and 2 were dried at 250° C. for 3 hours.

Subsequently, each of the catalysts was mixed with sufficient inert material (e.g. SiC) to assure proper plug flow conditions and loaded into a single tube test reactor of down flow mode ("Single Bed" comparative examples).

For preparing the "Stacked Bed" comparative examples, the catalysts (mixed with sufficient inert material) were loaded on top of each other into a single tube test reactor of down flow mode.

In total, two "Stacked Bed" comparative examples were prepared:
(a) 25% "ZSM-12"/75% "EU-2";
(b) 50% "ZSM-12"/50% "EU-2",
wherein "EU-2" refers to the catalyst of Example 2 and "ZSM-12" refers to the catalyst of Example 1.

Thus, e.g. 25% "ZSM-12"/75% "EU-2" means: 25% of the total dewaxing catalyst volume is occupied by the catalyst with ZSM-12 being located in the top of the stack, and 75% of the total dewaxing catalyst volume is occupied by the catalyst with EU-2 being located in the bottom of the stack.

Subsequently, a hydrogen partial pressure was applied of 140 bar and then the temperature was increased from room temperature to 125° C. at a rate of 20° C./h, and held for two hours. The temperature was increased further to 300° C. at a rate of 50° C./h, and held for 8 hours to ensure proper reduction of the metallic phase. The reactor was cooled to 200° C. and then the feed of Table 1 was introduced. After feed breakthrough, the temperature was increased to 250° C. in 4 hours, and held overnight.

The feed of Table 1 was added at a weight hourly space velocity of 1.2 kg $1^{-1}$ $h^{-1}$.

TABLE 1

| Feed | | |
|---|---|---|
| Density at 70/4° C. | g/ml | 0.8197 |
| Carbon content | wt. % | 85.99 |
| Hydrogen content | wt. % | 14.01 |
| Sulphur content, | wt. % | 0.001 |
| Nitrogen content, | ppmw | 0.0004 |
| UV Aromatics | | |
| Mono-aromatics | wt. % | 1.47 |
| Di-aromatics | wt. % | 0.17 |
| Tri-aromatics | wt. % | 0.09 |
| Tetra$^+$-aromatics | wt. % | 0.13 |
| Pour Point | ° C. | 42 |
| TBP-GLC | | |
| 0.5 wt. % recovery (IBP) | ° C. | 251 |
| 10 wt. % recovery | ° C. | 358 |
| 90 wt. % recovery | ° C. | 519 |
| 98 wt. % recovery | ° C. | 568 |
| 99.5 wt. % recovery | ° C. | 595 |

The performance of the single ZSM-12 and EU-2 catalysts and the ZSM-12/EU-2 catalyst stacks was evaluated at temperatures in the range between 330° C. and 350° C.

[Method: The performance of each catalyst bed was evaluated at temperatures in the range between 330° C. and 350° C. The performance of the catalyst beds was evaluated at a pour point improvement of 75° C., which means that the product has a pour point which is 75° C. lower than the pour point of the feedstock. The pour points are measured according to ASTM D97. The feed of Table 1 was added at a weight hourly space velocity of 1.2 kg $1^{-1}$ $h^{-1}$].

The performances of the single catalysts and the catalyst stacks are shown in FIG. 1.

In this FIGURE, the expression "wof %" represents the wt. % on feed. "C1-C4" represents the amount of product containing 1, 2, 3, or 4 carbons. "C5-150° C." represents the amount of a hydrocarbon product with carbon number 5 up to products that have a boiling point of 150° C. "150-370° C." represents the amount of product which has a boiling point in the range between 150 and 370° C. ">370° C." represents the amount of product which has a boiling point of 370° C. or higher as measured with ASTM D2887-93. "Treq.dPP 75° C." represents for the required reactor temperature to obtain a pour point (PP) improvement of 75° C.

In Table 2, the results are listed with their numerical values.

Example 4. Performance Testing of Comparative Mixed Bed Catalyst System

The catalysts of Examples 1 and 2 were dried at 250° C. for 3 hours. Subsequently, a mixture of 75% of the ZSM-12 based catalyst and 25% of the EU-2(ZSM-48) based catalyst was prepared. Then the ZSM-12/EU-2(ZSM-48) catalyst mixture was mixed with 0.1 mm SiC inert material in a 1:1 vol/vol ratio to assure proper plug flow conditions and carefully loaded into a single tube test reactor of down flow mode. This happened in a similar way as in Example 3, where the catalysts were loaded on top of each other. The total catalyst volume was 20 ml. Subsequently, a hydrogen partial was applied of 140 bar and then the temperature was increased from room temperature to 125° C. at a rate of 20°

C./h, and held for two hours. The temperature was increased further to 300° C. at a rate of 50° C./h, and held for 8 hours to ensure proper reduction of the metallic phase. The reactor was cooled to 200° C. and then the feed of Table 1 was introduced. After feed breakthrough, the temperature was increased to 250° C. in 4 hours, and held overnight.

The performance of the catalyst bed was evaluated according to the method described in Example 3.

The performance of the mixed catalyst bed is shown in FIG. 1. For an explanation of the numbers and abbreviations in the FIGURE, see Example 3.

In Table 2, the results are listed with their numerical values.

Example 5. Performance Testing of Catalyst System According to Present Invention Catalysts made in accordance with Examples 1 and 2 were dried at 250° C. for 3 hours.

A stacked system was prepared with, in the top layer, a physical mixture of 40% of the total "ZSM-12" catalyst and 10% of the total "EU-2" catalyst and, in the bottom layer, a physical mixture of 10% of the total "ZSM-12" catalyst and 40% of the total "EU-2" catalyst. That is to say, the top layer was an 80:20 mixture of "ZSM-12" catalyst:"EU-2" catalyst and the bottom layer was a 20:80 mixture of of "ZSM-12" catalyst:"EU-2" catalyst and the overall catalyst volume ratio was 50:50.

The total catalyst volume was 20 ml. Subsequently, a hydrogen partial was applied of 140 bar and then the temperature was increased from room temperature to 125° C. at a rate of 20° C./h, and held for two hours. The temperature was increased further to 300° C. at a rate of 50° C./h, and held for 8 hours to ensure proper reduction of the metallic phase. The reactor was cooled to 200° C. and then the feed of Table 1 was introduced. After feed breakthrough, the temperature was increased to 250° C. in 4 hours, and held overnight.

The performance of the catalyst bed was evaluated according to the method described in Example 3.

The performance of the catalyst bed is shown in FIG. 1. For an explanation of the numbers and abbreviations in the FIGURE, see Example 3.

In Table 2, the results are listed with their numerical values.

Conclusion

It can be concluded from the performance data of the Examples, that the catalyst system (i.e. the gradient mixed system) of the present invention exhibits an enhanced activity and an improved base oil yield not only when compared to a catalyst system containing only a EU-2 based catalyst but also when compared to a mixture of both ZSM-12 and EU-2 catalysts.

Further, the catalyst system of the present invention exhibits an improved base oil yield when compared to a catalyst system containing only a ZSM-12 based catalyst whereas the activity is very well comparable to or even better than a catalyst system containing only a ZSM-12 based catalyst.

The base oil yield of the catalyst system of the present invention is on par when compared with a stacked bed catalyst system having a ZSM-12 based catalyst in the top of the stack and a EU-2 based catalyst in the bottom of the stack, and the activity of the catalyst system of the present invention is also slightly higher.

TABLE 2

| | | FIG. 1 label | | | | | |
|---|---|---|---|---|---|---|---|
| | | Comparative Examples | | | | | Working Example 50% ZSM-12/50% |
| Catalyst Bed Arrangement | | 100% ZSM-12 Single Bed | 100% EU-2 Single Bed | 75% ZSM-12/25% EU-2 Stacked Bed | 75% ZSM-12/25% EU-2 mix Mixed Bed | 50% ZSM-12/50% EU-2 Stacked Bed | EU-2 gradient mix Present Invention |
| Treq. dPP 75° C. | ° C. | 336 | 342 | 332 | 335 | 335 | 334 |
| | | | | Yields: | | | |
| C1-C4 | wof % | 0.5 | 1.1 | 0.6 | 0.7 | 0.7 | 0.8 |
| C5-150° C. | wof % | 4.0 | 4.0 | 3.2 | 4.3 | 3.2 | 3.5 |
| 150-370° C. | wof % | 23.7 | 19.8 | 20.7 | 23.5 | 19.5 | 20.3 |
| >370° C. | wof % | 71.7 | 75.0 | 75.7 | 71.8 | 76.5 | 75.7 |

That which is claimed is:

1. A catalyst system for dewaxing of a hydrocarbon feedstock comprising a mixture of a first dewaxing catalyst composition and a second dewaxing catalyst composition, wherein the first dewaxing catalyst composition is a ZSM-12 zeolite based catalyst composition and the second dewaxing catalyst composition is a EU-2 and/or ZSM-48 zeolite based catalyst composition, and wherein a concentration gradient of the mixture is achieved within a single catalyst bed, such that the concentration of the first dewaxing catalyst is decreasing and the concentration of the second dewaxing catalyst is increasing through the catalyst bed.

2. The catalyst system according to claim 1, wherein the catalyst bed comprises two or more separate regions in a stacked configuration, each region comprising a mixture of the first and second dewaxing catalysts, such that the regions together define a gradient decreasing in the concentration of the first dewaxing catalyst and increasing in the concentration of second dewaxing catalyst composition in a step-wise, non-linear, fashion from one region to the next region through the catalyst bed.

3. The catalyst system according to claim 1, wherein the ZSM-12 zeolite is present in the first dewaxing catalyst composition in an amount of at least 10 wt. % and at most 70 wt. % and the first dewaxing catalyst composition further comprises a binder in an amount of at least 30 wt. % and no more than 90 wt. %, based on the dry weight of the first dewaxing composition.

4. The catalyst system according to claim 1, wherein the EU-2 and/or ZSM-48 zeolite is present in the second dewaxing catalyst composition in an amount of at least 15 wt. % and at most 70 wt. % and the second dewaxing catalyst composition further comprises a binder in an amount of at least 30 wt. % and no more than 85 wt. %, based on the dry weight of the second dewaxing composition.

5. The catalyst system according to claim 1, wherein the first dewaxing catalyst and the second dewaxing catalyst each comprise a noble metal component.

6. The catalyst system according to claim 1, wherein the ZSM-12 zeolite has a silica to alumina molar ratio of at least 50:1 and at most 250:1.

7. The catalyst system according to claim 1, wherein the EU-2 and/or ZSM-48 zeolite has a silica to alumina molar ratio of at least 60:1 and at most 300:1.

8. A process for dewaxing of a hydrocarbon feedstock comprising contacting a hydrocarbon feedstock with a catalyst system according to claim 1.

9. The process according to claim 8, wherein the process takes place at a temperature from 200° C. up to 450° C. and a pressure of from $5 \times 10^5$ to $200 \times 10^5$ Pa.

10. The process according to claim 8, wherein the hydrocarbon feedstock is a wax-containing feed that boils in the lubricating oil range having a 10% distillation point at 200° C. or higher, as measured by ASTM D-2887-93.

* * * * *